(12) United States Patent
Kennedy et al.

(10) Patent No.: US 6,579,499 B1
(45) Date of Patent: Jun. 17, 2003

(54) LIQUID COMPOUND PIN REPLICATOR WITH WEIGHT BIAS

(75) Inventors: Craig M. Kennedy, San Marcos, CA (US); Fernando J. Ramirez, Fountain Valley, CA (US)

(73) Assignee: Autosplice, Inc., San Diego, CA (US)

( * ) Notice: Subject to any disclaimer, the term of this patent is extended or adjusted under 35 U.S.C. 154(b) by 21 days.

(21) Appl. No.: 09/584,616

(22) Filed: May 31, 2000

(51) Int. Cl.[7] .............................. B01L 3/02; B01L 3/00; G01N 1/10; G01N 1/16; G01N 1/26; G01N 1/00
(52) U.S. Cl. .................. 422/100; 436/180; 422/99; 73/863.31; 73/863.32; 73/864; 73/864.01; 73/864.24; 73/864.31
(58) Field of Search .................. 422/100, 99; 436/180; 73/863.31, 863.32, 864, 864.01, 864.24, 864.31

(56) References Cited

U.S. PATENT DOCUMENTS

| | | | | |
|---|---|---|---|---|
| 3,568,735 A | * | 3/1971 | Lancaster | |
| 3,650,306 A | * | 3/1972 | Lancaster | |
| 4,106,911 A | * | 8/1978 | Marcelli | |
| 4,158,035 A | * | 6/1979 | Haase et al. | |
| 4,444,062 A | * | 4/1984 | Bennett et al. | |
| 4,498,510 A | * | 2/1985 | Mihshew, Jr. et al. | |
| 4,971,763 A | * | 11/1990 | Columbus | |
| 5,660,792 A | * | 8/1997 | Koike | |
| 5,756,050 A | * | 5/1998 | Ershow et al. | |
| 5,827,745 A | * | 10/1998 | Astle | |
| 5,882,930 A | * | 3/1999 | Baier | |
| 5,962,329 A | * | 10/1999 | Ershov et al. | |
| 5,976,470 A | * | 11/1999 | Maiefski et al. | |
| 6,024,925 A | | 2/2000 | Little et al. | ............ 422/100 |
| 6,051,190 A | * | 4/2000 | Birch et al. | |
| 6,238,626 B1 | * | 5/2001 | Higuchi et al. | |
| 6,255,119 B1 | * | 7/2001 | Baier | |
| 6,258,324 B1 | * | 7/2001 | Yiu | |
| 6,309,891 B1 | * | 10/2001 | Shalon et al. | |
| 2001/0008615 A1 | * | 7/2001 | Little et al. | |
| 2001/0019845 A1 | * | 9/2001 | Bienert et al. | |
| 2001/0049149 A1 | * | 12/2001 | Kennedy et al. | |
| 2002/0009392 A1 | * | 1/2002 | Wolk et al. | |
| 2002/0064887 A1 | * | 5/2002 | Shalon et al. | |

* cited by examiner

*Primary Examiner*—Jill Warden
*Assistant Examiner*—Brian R. Gordon

(57) ABSTRACT

A pin replicator is disclosed for dispensing minute volumes of liquid onto a substrate surface in an array in connection with drug discovery, diagnostic analysis, and other applications. The pin replicator comprises a base plate, a plurality of pins reciprocable through corresponding holes in the base plate, and a free floating weight plate resting on top of the upper ends of the pins. The weight plate biases the pins toward their fully extended lowered positions. A cover attaches to the base plate, encloses the pins and weight plate and guides the weight plate during vertical movement thereof. The pin replicator can be moved downwardly toward a first micro titer plate so that a lower end of each of the pins contacts the sample liquid in the corresponding well a sufficient amount to pick up and retain a small quantity of the sample liquid due to surface tension. The pin replicator can thereafter be moved downwardly toward a second micro titer plate so that the lower end of each of the pins is sufficiently close to a corresponding well of the second micro titer plate so that the small quantity of the sample liquid on the lower end of each of the pins contacts an upper surface of the corresponding well of the second micro titer plate.

20 Claims, 2 Drawing Sheets

US 6,579,499 B1

LIQUID COMPOUND PIN REPLICATOR WITH WEIGHT BIAS

BACKGROUND OF THE INVENTION

The present invention relates to methods and apparatus for preparing liquid compounds for chemical and biological analysis, and more particularly, to equipment for dispensing minute volumes of liquid onto a substrate surface in an array in connection with drug discovery and diagnostic analysis.

As the field of biotechnology has developed, traditional techniques for analyzing chemical structures, such as the use of pipettes to manually deposit small amounts of liquid, have become impractical. Automated devices have been developed, for example, to permit parallel processing protocols for DNA diagnostics. In one form of such a device a matrix of individual pins is attached to a robotic arm. The spacing of the pins is sufficient to allow their terminal lower ends to be dipped into corresponding wells of a micro titer plate, thereby wetting the end of each pin with the sample liquid. The robotic arm then moves the pin matrix to the surface of a target substrate and contacts the end of each pin with the surface. The target substrate surface can either be flat or configured to provide a plurality of liquid receiving vessels or wells. The continual contact of the delicate pins to the substrate surface leads to wear which can introduce errors. U.S. Pat. No. No. 6,024,925 assigned to Sequenom, Inc. of San Diego discloses an improved pin replicator that uses individually spring biased hollow pins. However, the structure of the Sequenom pin replicator is relatively complex, unduly expensive and subject to mechanical failures.

SUMMARY OF THE INVENTION

It is therefore the primary object of the present invention to provide an improved pin replicator for dispensing minute volumes of liquid onto a substrate surface in an array in connection with drug discovery, diagnostic analysis, and other applications.

In accordance with the present invention, a pin replicator comprises a base plate, a plurality of pins reciprocable through corresponding holes in the base plate, and a free floating weight plate resting on top of the upper ends of the pins. The weight plate biases the pins toward their fully extended lowered positions. A cover attaches to the base plate, encloses the pins and weight plate and guides the weight plate during vertical movement thereof. The pin replicator can be moved downwardly toward a first micro titer plate so that a lower end of each of the pins contacts the sample liquid in the corresponding well a sufficient amount to pick up and retain a small quantity of the sample liquid due to surface tension. The weight plate serves to ensure co-planarity of the lower ends of the pins by pushing each pin downwardly to their fully extended lowered positions while allowing each pin to move upwardly should it contact an upper surface of the corresponding well of the first micro titer plate. The pin replicator can be moved upwardly away from the first micro titer plate and laterally to a position above a second micro titer plate. The pin replicator can then be moved downwardly toward the second micro titer plate so that the lower end of each of the pins is sufficiently close to a corresponding well of the second micro titer plate so that the small quantity of the sample liquid on the lower end of each of the pins contacts an upper surface of the corresponding well of the second micro titer plate. Thereafter the pin replicator can be moved upwardly away from the second micro titer plate and surface tension will cause a portion of the small quantity of the sample liquid previously carried by the lower end of each of the pins to remain in the corresponding well of the second micro titer plate.

DESCRIPTION OF THE PREFERRED EMBODIMENTS

Figure 1:
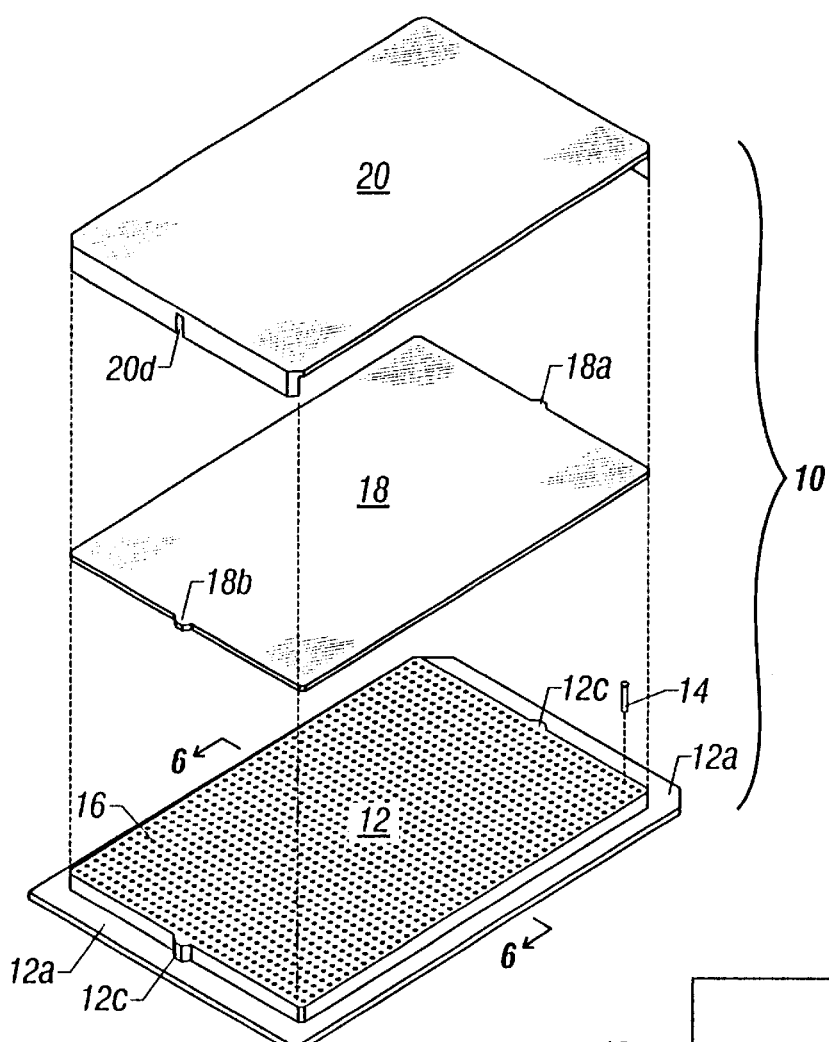
FIG. 1 is an exploded perspective view of a preferred embodiment of the pin replicator of the present invention.
Figure 2:
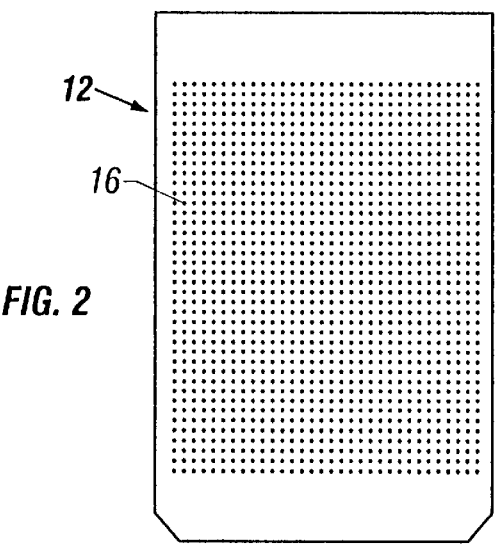
FIG. 2 is a plan view of the base plate of the pin replicator of FIG. 1.

Referring to FIG. 1, a generally planar pin replicator 10 comprises a base plate 12, a plurality of pins 14 reciprocable through corresponding holes 16 in the base plate 12, and a free floating weight plate 18 resting on top of the upper ends of the pins 14. The weight plate 18 biases the pins 14 toward their fully extended lowered positions. A cover 20 attaches to the base plate 12, encloses the pins 14 and weight plate 18 and guides the weight plate 18 during vertical movement thereof. The base plate 12, weight plate 18 and cover 20 each have a generally rectangular configuration. These components are preferably made of a suitable thermoplastic material so that they can be injection molded to provide the desired shape and dimensions. As shown in FIG. 2, the base plate 12 may have holes 16 across substantially its entire surface to accommodate a large number of pins 14, such as one thousand two hundred and eighty pins. Alternatively, as show in FIG. 1, only the ends of the base plate 12 need have holes 16 formed therein to accommodate a smaller number of pins 14, such as two hundred and fifty-six pins 14.

Figure 4:
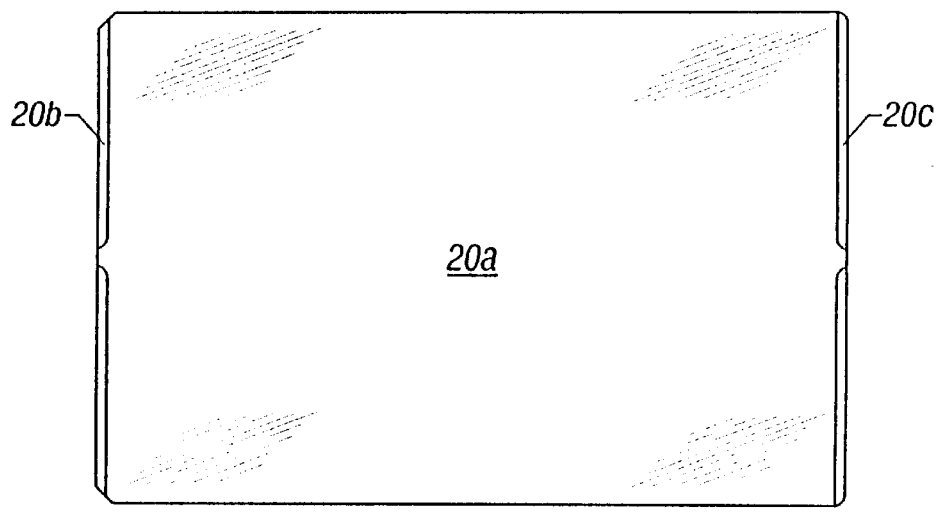
FIG. 4 is an enlarged plan view of the cover of the pin replicator of FIG. 1.
Figure 5:
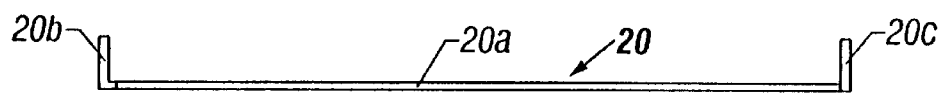
FIG. 5 is an enlarged side elevation view of the cover of the pin replicator of FIG. 1.

The array of holes 16 in the base plate 12 provides a predetermined pattern of rows and columns. A periphery 12a (FIG. 1) of the base plate 12 extends beyond the cover 20 to provide a flange for predetermined alignment of the pin replicator in a receptacle in a jig or automated system (not shown) into which the pin replicator 10 can be loaded. The cover 20 includes a main horizontal. section 20a (FIGS. 4 and 5) with two smaller vertical end walls 20b and 20c at each end. Preferably the medial portion 12b (FIG. 1) of the base plate 12 is raised compared to the periphery 12a to provide a shoulder over which the end walls 20b and 20c of the cover 20 may be snap fit to retain the base plate 12 and cover 20 together.

Figure 3:
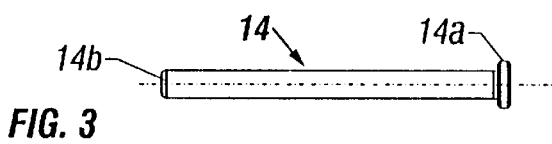
FIG. 3 is an enlarged side elevation view of one of the headed pins of the pin replicator of FIG. 1.

The upper end of each pin 14 (FIG. 3) comprises a head 14a that abuts the base plate 12 when the pin 14 is in its fully extended lowered position. The lower end 14b of each pin 14 is tapered to facilitate insertion through the corresponding hole 16 in the base plate 12. The weight plate 18 and the cover 20 include complementary projections and registration features that engage each other to guide the weight plate. These complementary projections and registration features include tabs 18a (FIG. 1) formed on the weight plate 18 and slots 20d (FIG. 4) formed on the cover 20 which slidingly receive the tabs 18a. The base plate 12 also has tabs 12c that engage the cover 20 to align the same.

Figure 6:
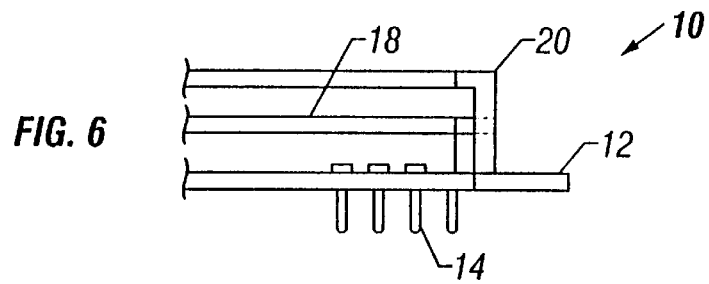
FIG. 6 is an enlarged fragmentary vertical sectional view of the pin replicator taken along line 6—6 of FIG. 1.

FIG. 6 is an enlarged fragmentary vertical sectional view of the pin replicator 10 taken along line 6—6 of FIG. 1. The pins 14 are shown in their fully extended lowered positions. However, the weight plate 18 is shown slightly raised off of the heads 14a of the pins for the sake of clarity.

Figure 7:
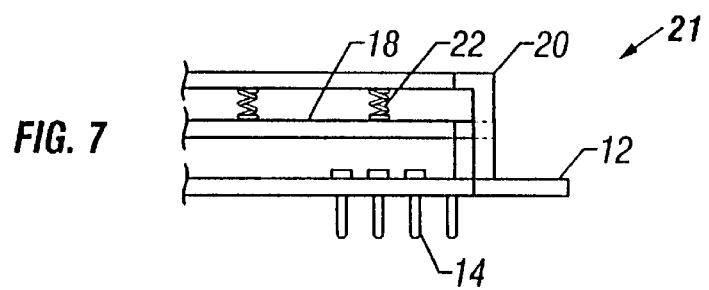
FIG. 7 is a view similar to FIG. 6 showing an alternate embodiment of the pin replicator that includes coil springs for biasing its weight plate toward its base plate.

FIG. 7 illustrates an alternate embodiment 21 of the pin replicator in which at least one coil spring 22 positioned between the weight plate 18 and the cover 20 for biasing the weight plate toward the base plate 12. This provides the advantage of allowing the pin replicator to be inverted without the pins moving away from their fully extended positions.

Our replicator can be used in a manually operable jig or in an advanced computer-controlled robotic system. It can be inexpensively manufactured so that it can be made disposable. Alternatively, it may be made of stainless steel components so that it can be washed, sterilized, and re-used.

In accordance with a novel liquid transfer method provided by the present invention, the pin replicator 10 can be moved downwardly toward a first micro titer plate (not shown) so that a lower end 14b of each of the pins 14 contacts the sample liquid in the corresponding well a sufficient amount to pick up and retain a small quantity of the sample liquid due to surface tension. The weight plate 18 serves to ensure co-planarity of the lower ends 14b of the pins 14 by pushing each pin 14 downwardly to its fully extended lowered position while allowing each pin 14 to move upwardly should it contact an upper surface of the corresponding well of the first micro titer plate. The pin replicator 10 can be moved upwardly away from the first micro titer plate and laterally to a position above a second micro titer plate (not shown). The pin replicator 10 can then be moved downwardly toward the second micro titer plate so that the lower end 14b of each of the pins 14 is sufficiently close to a corresponding well of the second micro titer plate so that the small quantity of the sample liquid on the lower end 14b of each of the pins 14 contacts an upper surface of the corresponding well of the second micro titer plate. Thereafter the pin replicator 10 can be moved upwardly away from the second micro titer plate and surface tension will cause a portion of the small quantity of the sample liquid previously carried by the lower end 14b of each of the pins 14 to remain in the corresponding well of the second micro titer plate.

Thus, an aspect of the invention provides a base plate having an array of holes that extend therethrough; a plurality of discrete pins, each pin having an upper end and a lower end and being freely slidingly received in a corresponding hole in the base plate for independent reciprocating motion between a fully extended lowered position and a predetermined retracted raised position; and a free floating weight plate resting on the upper ends of the pins to bias the pins toward the fully extended lowered position with means for guiding the weight plate during vertical movement thereof.

While we have described preferred embodiments of our novel pin replicator and liquid transfer method, it should be apparent to those having ordinary skill in the art that our invention can be modified in both arrangement and detail. For example, the pattern of the pins 14 can be varied. The pins 14 could be hollow and they can be made of metal or plastic, or any other suitable material. The pin replicator 10 need not be used with micro titer plates but can be used with any source and target suitable for maintaining the separate physical integrity of the different liquid samples. Therefore, the protection afforded our invention should only be limited in accordance with the scope of the following claims.

We claim:

1. A pin replicator, comprising:
    a base plate having an array of holes that extend therethrough;
    a plurality of discrete pins, each pin having an upper end and a lower end and being freely slidingly received in a corresponding hole in the base place for independent reciprocating motion between a fully extended lowered position and a predetermined retracted raised position;
    a free floating weight plate resting on the upper ends of the pins to bias the pins toward the fully extended lowered position; and
    means for guiding the weight plate during vertical movement thereof.

2. The pin replicator of claim 1 wherein the upper end of each pin comprises a head that abuts the base plate when the pin is in its fully extended lowered position.

3. The pin replicator of claim 1 wherein the array of holes provides a pattern of rows and columns of pins.

4. The pin replicator of claim 1 wherein the base plate and the weight plate each have a generally rectangular configuration.

5. A pin replicator, comprising:
    a base plate having an array of holes that extend therethrough;
    a plurality of pins, each pin having an upper end and a lower end and being slidingly received in a corresponding hole in the base place for reciprocating motion between a fully extended lowered position and a predetermined retracted raised position;
    a free floating weight plate resting on the upper ends of the pins to bias the pins toward the fully extended lowered position; and
    a cover attached to the base plate and enclosing the weight plate, the cover being configured to engage and guide the weight plate during vertical movement thereof.

6. The pin replicator of claim 5 wherein the upper end of each pin comprises a head that abuts the base plate when the pin is in its fully extended lowered position.

7. The pin replicator of claim 5 wherein the array of holes provides a pattern of rows and columns of pins.

8. The pin replicator of claim 5 wherein a periphery of the base plate extends beyond the cover to provide a flange for predetermined alignment of the pin replicator in a receptacle.

9. The pin replicator of claim 5 wherein the weight plate and the cover include complementary projections and registration features that engage each other to guide the weight plate.

10. The pin replicator of claim 9 wherein the complementary projections and registration features include tabs formed on the weight plate and slots formed on the cover which slidingly receive the tabs.

11. The pin replicator of claim 5 and further comprising spring means for biasing the weight plate downwardly.

12. The pin replicator of claim 5 wherein the spring means includes at least one coil spring positioned between the weight plate and the cover.

13. The pin replicator of claim 5 wherein the base plate and the weight plate each have a generally rectangular configuration.

14. A pin replicator, comprising:
    a base plate having an array of holes that extend therethrough;

a plurality of pins, each pin having an upper end and a lower end and being slidingly received in a corresponding hole in the base place for reciprocating motion between a fully extended lowered position and a predetermined retracted raised position;

a free floating weight plate resting on the upper ends of the pins to bias the pins toward the fully extended lowered position; and means for guiding the weight plate during vertical movement thereof, said means for guiding including a cover attached to the base plate and enclosing the weight plate.

15. The pin replicator of claim 14, wherein a periphery of the base plate extends beyond the cover to provide a flange for predetermined alignment of the pin replicator in a receptacle.

16. The pin replicator of claim 14, wherein the weight plate and the cover include complementary projections and registration features that engage each other to guide the weight plate.

17. The pin replicator of claim 16 wherein the complementary projections and registration features include tabs formed on the weight plate and slots formed on the cover which slidingly receive the tabs.

18. The pin replicator of claim 14, further comprising spring means including at least one coil spring positioned between the weight plate and the cover.

19. A method of transferring minute quantities of a sample liquid from a source to a target substrate for further analysis, comprising the steps of:

providing a first micro titer plate having an array of wells each including a corresponding sample liquid;

providing a generally planar pin replicator having an array of vertically reciprocable pins biased to a lowered extended position by a weight plate, the array of pins being dimensioned and configured to be complementary to the array of wells on the first micro titer plate;

positioning the pin replicator horizontally above the first micro titer plate;

moving the pin replicator downwardly toward the first micro titer plate so that a lower end of each of the pins contacts the sample liquid in the corresponding well a sufficient amount to pick up and retain a small quantity of the sample liquid due to surface tension, the weight plate serving to ensure co-planarity of the lower ends of the pins by pushing each pin downwardly to a fully extended lowered position while allowing each pin to move individually upwardly should it contact an upper surface of the corresponding well of the first micro titer plate;

moving the pin replicator upwardly away from the first micro titer plate;

moving the pin replicator laterally to a horizontal position above a second micro titer plate having an array of wells corresponding in location and arrangement to the array of pins;

moving the pin replicator downwardly toward the second micro titer plate so that a lower end of each of the pins is sufficiently close to a corresponding well of the second micro titer plate so that the small quantity of the sample liquid on the lower end of each of the pins contacts an upper surface of the corresponding well of the second micro titer plate; and moving the pin replicator upwardly away from the second micro titer plate;

whereby surface tension will cause a portion of the small quantity of the sample liquid previously carried by the lower end of each of the pins to remain in the corresponding well of the second micro titer plate.

20. A pin replicator, comprising:

a base plate having an array of holes that extend therethrough;

a plurality of pins, each pin having an upper end and a lower end and being slidingly received in a corresponding hole in the base place for reciprocating motion between a fully extended lowered position and a predetermined retracted raised position;

a free floating weight plate resting on the upper ends of the pins to bias the pins toward the fully extended lowered position;

means for guiding the weight plate during vertical movement thereof; and spring means for biasing the weight plate downwardly.

* * * * *